(12) United States Patent
Vagt et al.

(10) Patent No.: US 8,739,409 B2
(45) Date of Patent: Jun. 3, 2014

(54) METHOD FOR DUAL PRODUCTION OF SMALL-SCALE PRODUCTS

(75) Inventors: Carsten Vagt, Oyten (DE); Ralf Wehning, Grasberg (DE)

(73) Assignee: BEGO Medical GmbH, Bremen (DE)

( * ) Notice: Subject to any disclaimer, the term of this patent is extended or adjusted under 35 U.S.C. 154(b) by 769 days.

(21) Appl. No.: 13/003,279

(22) PCT Filed: Jul. 2, 2009

(86) PCT No.: PCT/EP2009/058367
§ 371 (c)(1),
(2), (4) Date: Mar. 16, 2011

(87) PCT Pub. No.: WO2010/003882
PCT Pub. Date: Jan. 14, 2010

(65) Prior Publication Data
US 2011/0170977 A1     Jul. 14, 2011

(30) Foreign Application Priority Data
Jul. 8, 2008   (DE) .......................... 10 2008 031 925

(51) Int. Cl.
| | |
|---|---|
| *A61C 5/10* | (2006.01) |
| *B23P 13/04* | (2006.01) |
| *G06F 19/00* | (2011.01) |
| *B23B 37/00* | (2006.01) |
| *B29C 35/08* | (2006.01) |

(52) U.S. Cl.
USPC .......... 29/896.1; 29/527.1; 29/527.2; 29/557; 29/592; 433/201.1; 700/118; 264/139; 264/113; 264/161; 264/162; 264/163; 264/308; 264/401; 264/460; 264/463; 264/497

(58) Field of Classification Search
CPC .... A61C 13/08; A61C 13/081; A61C 13/087; A61C 13/0013; A61C 13/0018; B22F 3/105; B22F 3/1055; B22F 2003/1058; B29C 67/0088; B29C 67/0092; B29C 67/0074; B29C 67/0077; G05B 2219/49018

USPC .......... 29/896.1, 592, 557; 700/118; 433/201.1; 264/139, 113, 161, 162, 264/163, 308, 401, 460, 463, 497
See application file for complete search history.

(56) References Cited

U.S. PATENT DOCUMENTS 6,682,684 B1 *   1/2004   Jamalabad et al. ........... 264/308
(Continued)

FOREIGN PATENT DOCUMENTS

DE          195 33 960 C2       8/1997
(Continued)

OTHER PUBLICATIONS

The International Search Report for Application No. PCT/EP2009/058367, dated Jan. 15, 2010, 7 pages.
(Continued)

*Primary Examiner* — Sarang Afzali
(74) *Attorney, Agent, or Firm* — Kilpatrick Townsend and Stockton LLP

(57) ABSTRACT

The invention relates to a method for manufacturing products by applying material at least partially in layers to form a structure, in particular by selective laser melting (SLM), said method comprising the steps of: (a) providing a base plate, (b) applying a layer of a curable material, (c) selectively curing predetermined zones of the applied layer on the basis of geometrical data of the product, (d) repeating steps (b) and (c) until the geometry of a first partial volume of the product has been created in the form of a cured material and (e) removing the uncured material. According to the invention, a reference mark is provided, the unit formed by the base plate and the first volume zones is clamped into a specific position by means of the reference mark and the respective second partial volume of the respective product is cut from the base plate, preferably by machining, in particular CNC milling.

9 Claims, 1 Drawing Sheet

(56) References Cited

U.S. PATENT DOCUMENTS

| | | | |
|---|---|---|---|
| 6,994,549 B2 * | 2/2006 | Brodkin et al. | 433/202.1 |
| 7,003,864 B2 * | 2/2006 | Dirscherl | 29/527.2 |
| 7,084,370 B2 * | 8/2006 | Hagemeister et al. | 219/121.85 |
| 7,172,724 B2 * | 2/2007 | Abe et al. | 419/6 |
| 7,261,550 B2 * | 8/2007 | Herzog | 425/547 |
| 2002/0129485 A1 * | 9/2002 | Mok et al. | 29/527.2 |
| 2003/0094259 A1 | 5/2003 | Siedal | |
| 2004/0021256 A1 * | 2/2004 | DeGrange et al. | 264/497 |
| 2005/0029711 A1 * | 2/2005 | Abe et al. | 264/497 |
| 2006/0131770 A1 * | 6/2006 | Dierkes et al. | 264/16 |
| 2007/0173967 A1 * | 7/2007 | Kritchman et al. | 700/119 |

FOREIGN PATENT DOCUMENTS

| | | |
|---|---|---|
| DE | 198 53 978 C1 | 5/2000 |
| DE | 199 05 067 A1 | 8/2000 |
| DE | 101 24 795 A1 | 12/2002 |
| DE | 103 20 085 A1 | 2/2004 |
| DE | 102 19 983 B4 | 3/2004 |
| DE | 299 24 924 U1 | 12/2006 |
| DE | 10 2005 050 665 A1 | 4/2007 |
| DE | 11 2006 001 961 T5 | 5/2008 |
| EP | 1 348 506 A2 | 10/2003 |
| EP | 1 464 298 A2 | 10/2004 |
| EP | 1 568 472 B1 | 2/2005 |
| EP | 0 734 842 B2 | 5/2006 |
| EP | 1 021 997 B1 | 5/2007 |
| EP | 1 974 688 A1 | 10/2008 |
| WO | WO 2004-004955 A1 | 1/2004 |
| WO | WO 2005-080029 A1 | 9/2005 |

OTHER PUBLICATIONS

The International Written Opinion for Application No. PCT/EP2009/058367, dated Jan. 15, 2010, 8 pages.

* cited by examiner

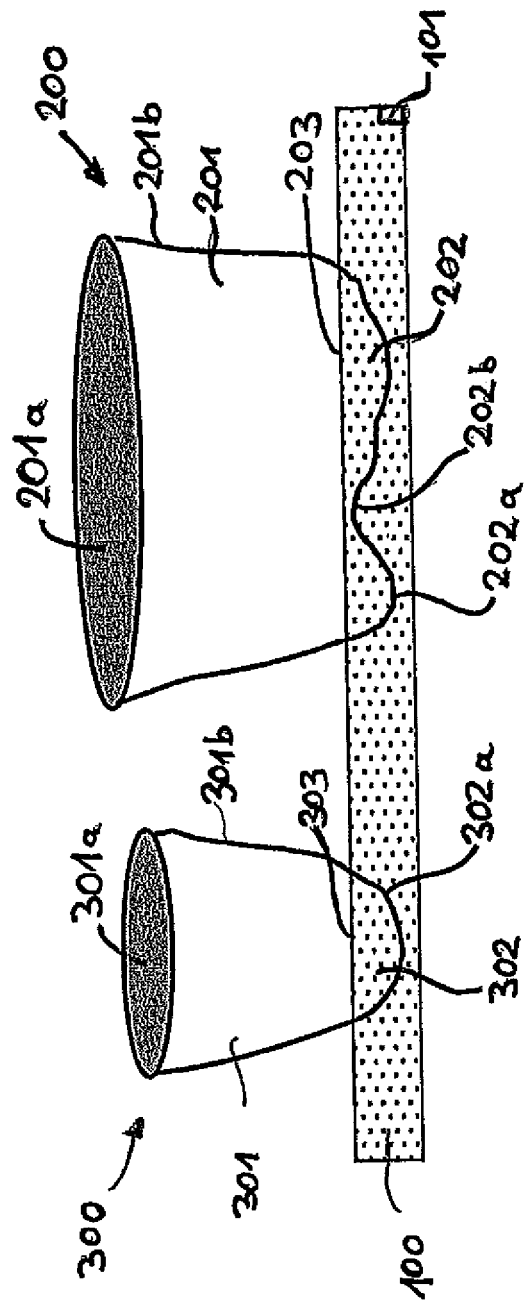

METHOD FOR DUAL PRODUCTION OF SMALL-SCALE PRODUCTS

CROSS-REFERENCE TO RELATED APPLICATIONS

This application is a National Stage of International Application No. PCT/EP2009/058367, filed Jul. 2, 2009, which claims the benefit of priority to German Application No. 10 2008 031 925.2, filed Jul. 8, 2008, the disclosures of each are herein incorporated by reference.

The invention relates to a method for manufacturing products by applying material at least partially in layers to form a structure, in particular by selective laser melting (SLM), said method comprising the steps of:

(a) providing a base plate,
(b) applying a layer of a curable material,
(c) selectively curing predetermined zones of the applied layer on the basis of geometrical data of the product,
(d) repeating steps (a) and (b) until the geometry of a first partial volume of the product has been created in the form of cured material,
(e) removing the uncured material.

The invention also relates to a device for manufacturing products by applying material in layers, comprising means for applying a layer of a curable material to a base plate and means for selectively curing predetermined zones of the applied layer on the basis of geometrical data of the products.

Another aspect of the invention relates to a device arrangement for manufacturing products by applying material partially in layers, comprising a device for forming the products by layered application of material, comprising means for applying a layer of a curable material to a base plate and means for selectively curing predetermined zones of the applied layer on the basis of geometrical data of the products.

Methods and devices for manufacturing products by applying material in layers are known, for example, from DE 299 24 924 U1, EP 1 021 997 B1, DE 102 19 983 B4, DE 103 20 085 A1, EP 1 464 298 B1, WO 2005/080029 A1, EP 1 568 472 B1 and DE 10 2005 050 665 A1. Methods of the kind initially specified allow geometrically complex products to be manufactured efficiently. Methods of the kind initially specified are known from "rapid prototyping", for example, in which a product model that can be used for demonstration and testing is made directly from product geometry data which describe the three-dimensional shape of the product.

US 2003/0094 259 A1 discloses a method and an apparatus for production of high-strength metal structures, in which a structure is constructed in layers on a support plate by melting a metal wire onto it with an electron or laser beam.

In DE 198 53 978 C1, a selective laser sintering device for producing a molded body by means of a grinding device is shown, with which the surface of the molded body under construction can be smoothed.

An apparatus and method for producing a three-dimensional object by successive curing of layers by sintering a powdery material are known from EP 0 734 842 B2. A prefabricated plate made of cured material is used as a base for the object to be formed.

DE 195 33 960 C2 discloses a method and an apparatus for making metal workpieces, in which metal-containing powder is melted in layers by a laser beam, and applied layers are subsequently machined with precision milling or grinding tools.

DE 101 24 795 A1 shows a method and an apparatus for producing a workpiece by successive curing of horizontally applied powdery starting material, in which the surface is finely machined after a specific number of layers have been completed.

DE 199 05 067 A1 discloses an apparatus for producing a molded body by layered application of powdery material, with a support for the layered structure, in which irregularities in the last layer to be irradiated are ground away at least partially by means of a grinding device.

DE 11 2006 001 961 T5 shows a device for forming a layered object, in which a three-dimensional structure is formed on a base and subsequently removed from the base.

Creating a first layer on a substrate plate in direct selective laser sintering and joining the material of the first layer to the substrate plate by metallurgical fusion so that the substrate plate can be used as part of the component is known from Wilhelm Meiners *Direktes Selektives Laser Sintern einkomponentiger metallischer Werkstoffe*, Aachen: Shaker, 1999, pp. 107-111, ISBN 3-8265-6571-1.

Methods of the kind initially specified may be carried out, for example, with a powdery or other free-flowing material which can be hardened by a chemical cross-linking reaction or a physical bonding process, for example fusion or sintering, and in this way can produce a resilient three-dimensional structure. Preferred methods include selective laser sintering (SLS), for example, or selective laser melting (SLM). In other applications, a liquid curable material is used which can be selectively cured by photopolymerization by means of a laser beam, for example. For products to be used in dental technology, the selective laser melting (SLM) method is preferentially used for applying material in layers.

In methods of the kind initially specified, the product to be made is evenly spaced apart from the base plate and joined to the base plate by an auxiliary construction in the form of a spacer in order to facilitate subsequent detachment of the product. This spacer is itself made by layered curing of the starting material before the actual product is made. To this end, it is firstly necessary to determine the geometry and arrangement of the spacer in relation to the product to be manufactured. After manufacturing the product, the product must be separated from the base plate and from the spacer. This is usually done by forming predetermined breaking points in the spacer for the base plate and for the product. Depending on the geometry of the product to be manufactured, other supports similar to the spacer may be necessary to support the product during production. Said supports must firstly be computed and produced, and subsequently removed and disposed of. The methods initially specified can therefore be further improved in respect of production time, production costs and product quality.

A method for manufacturing implant abutments is known from EP 1 464 298 B1, in which powdery material is sintered or melted in layers onto a prefabricated base member by laser sintering and/or laser melting in order to form a main body joined to the base member. By this means, customized main bodies can be constructed on prefabricated, standardized base members. However, the use of prefabricated, standardized base members is only efficient if large quantities are made. This solution also requires dental parts that have a prefabricated base member.

In direct selective laser sintering, joining the first layer of material to be cured to the substrate plate by metallurgical fusion is known from Wilhelm Meiners: *"Direktes Selektives Laser Sintern einkomponentiger metallischer Werkstoffe"*, pp. 107-111, in which, owing to this fixed attachment, the substrate plate can be used as part of the component if the geometry of the component so permits. The aim is to reduce the construction time. A disadvantage of this solution also is that it can only be used for products whose geometry includes a plate-type base member that can be formed by a prefabricated substrate plate.

EP 0 734 842 B2 discloses a method for manufacturing a three-dimensional object, in which the object is constructed on a pre-sintered plate made of the same material as the object. After the construction process, the object is separated from the plate with a saw and post-processed. If the object has a planar base surface, the pre-sintered plate may alternatively become a part of the sintered object. The plate is sawed to the right shape with a jig saw and can no longer be used for a new construction process. The large amount of material lost as a result has a detrimental effect on production costs. Another disadvantage is that this approach is likewise only suitable for products having geometries than can be reproduced by the base plate, i.e., which have a planar base surface at least. However, complex geometries of the kind that are often found in individually fitted dental parts cannot be produced with prior art methods in which the base plate is integrated into the product to be manufactured.

The object of the invention is therefore to provide a method for manufacturing a product by applying material at least partially in layers, and with which the product quality, in particular of products with complex geometries, can be further improved.

This object is achieved according to the invention by a method for manufacturing products by applying material at least partially in layers, in particular by selective laser melting, said method comprising the steps of:

(a) providing a base plate (100) made of the same material as the product,
(b) applying a layer of a curable material,
(c) selectively curing predetermined zones of the applied layer on the basis of geometrical data of at least two separate products,
(d) repeating steps (b) and (c) until the geometry of a respective first partial volume of the respective product has been created in the form of cured material,
(e) removing the uncured material,
   wherein a respective second partial volume of each product is formed as a volume zone of the base plate,
and further comprising the steps:
   providing a reference mark,
   clamping the unit formed by the base plate and the first volume zone into a specific position by means of the reference mark,
   cutting the respective second partial volume of the product from the base plate, preferably by machining, in particular by CNC milling.

According to the invention, the products or a respective first partial volume of the products are formed by layered application of material to a base plate that already consists of the material from which the products or a respective partial volume of the respective product is manufactured by applying material in layers, i.e., by applying a curable material in layers and selectively curing the layers thus applied. In the cured state, therefore, the base plate and the product geometries produced by applying material in layers consist of the same material.

The layered construction of the products or of a respective first partial volume of the products can begin directly on a base plate made of the same material as the cured products, with the products or a respective first partial volume of the products having to be spaced apart from the base plate by a spacer or the like, and without all the disadvantages this would involve. The respective first partial volume of the products produced on the base plate by layered application of material is therefore integral with the base plate.

The respective first partial volume of a plurality of identical or different products are formed simultaneously or successively on a shared base plate and spaced-apart from each other. At the end of the process, two or more individual products are then obtained which can be used independently of each other.

When the method is applied in the field of dental technology, biocompatible materials are the preferred materials for the base plate and for the layered structure.

According to the invention, only one respective first partial volume of the respective product is produced on the base plate by layered application of material, and a respective second partial volume of the respective product is defined as part of the base plate. A partial volume of a product is a three-dimensional section of the product, which forms the product in combination with one or more other partial volumes. The second partial volume of a product may be a contiguous volume zone of the base plate or may comprise two or more volume zones of the base plate. A respective first and second partial volume jointly form an integral product. The second partial volume of said product is "sunk" into the base plate, so to speak.

The method according to the invention further comprises the step of clamping the unit formed by the base plate and the first volume zones into a specific position by means of a reference mark.

The reference mark may be one or more reference points, for example, or one or more reference areas that are used to define clearly the position of the base plate and/or the products in space, preferably during layered application of material to form the respective first partial volume of the products and also when cutting the respective second partial volume of the products from the base plate. In particular when cutting the respective second partial volume of the products from the base plate, it is important that the coordinates of the products can be clearly identified to ensure that the respective second partial volume of the respective product which has been cut out exactly matches the predefined contour of the respective first partial volume of the respective product.

The method according to the invention also includes the step of cutting the respective second partial volume of the respective products from the base plate. It is particularly preferred that the respective second partial volume of the product is cut from the base plate by machining, in particular by milling.

After the geometry of the respective first partial volume of the respective product has been fully created as a cured material, the respective product is integrally embodied with the base plate. The respective second partial volume of the respective product is embodied as a volume zone of the base plate, i.e., other volume zones of the base plate that do not belong to any of the products connect the products to each other. In order to obtain the respective finished product, the respective second partial volume of the respective product should preferably be separated from the volume zones of the base plate which do not belong to the respective product.

The invention is also based on the realization that the dimensional accuracy that can be achieved for products by layered application of material is limited, and that it is dependent, for example, on the particle size of the material used, the layer thickness and/or the process control. By machining, in contrast, it is possible to achieve substantially higher levels of dimensional accuracy. The invention allows the respective second partial volume of the respective product to be cut out by removing that part of the base plate which does not belong to the product from the respective second partial volume of the respective product, by means of machining. This can be carried out by milling, preferably. In dental technology specifically, the preferred method for this is high-speed cutting (HSC), since the latter is particularly suitable for applications in which a high level of machining performance and high standards of surface quality are required, as is the case in dental technology. However, the zones of the base plate which do not form the respective second partial volume of the respective product can also be removed by electric discharge machining, turning, grinding, etc.

The method according to the invention has the advantage that cutting the respective second partial volume of the products from the base plate can be carried out with a substantially higher degree of dimensional accuracy than by applying layers of material to form the respective second partial volume of the products. It is particularly preferred in this regard that the partial volume of the respective product defined as a respective second partial volume is the one in which the surface of part of the surface must satisfy particularly high standards in respect of dimensional accuracy, contour accuracy and surface quality. In the field of dental technology, examples of such surfaces are masticating surfaces, reduced masticating surfaces, surfaces contacting an implant, and similar surfaces. The entire occlusal inner contour of a dental part preferably lies as a surface of the respective second partial volume inside the base plate, in order to ensure that the contour is produced with a high degree of dimensional accuracy, contour accuracy and surface quality.

The advantages of the respective method can be exploited by the inventive combination of layered construction steps and machining steps in a dual manufacturing process. On the one hand, the method for manufacturing a product by applying material in layers permits efficient manufacturing of products with complex geometries, such as products with hollow structures, hollow bodies or partial volumes with specific porosities for optimizing weight and/or strength. Machining, on the other hand, makes it possible to manufacture solid product parts and product surfaces with a high level of dimensional accuracy, contour accuracy and surface quality.

The invention is preferably characterized in that one or more tooth replacement parts are manufactured, and that the respective second partial volume of one or more of the tooth replacement parts comprises occlusal product segments, in particular masticating surfaces.

In the field of dental technology, highly resilient products with complex geometries, small dimensions and simultaneously with very small dimensional tolerances are often required. For example, occlusal surfaces of dental parts, especially, such as masticating surfaces, reduced masticating surfaces, etc., must be manufactured to high standards of dimensional accuracy, contour accuracy and surface quality.

For this reason, the respective second partial volume of the respective tooth replacement part or product preferably comprises product sections that usually necessitate the use of supports when prior art methods are applied. In the field of dental technology, such product sections may be caps, crowns or occlusal surfaces, i.e., product sections adapted as masticating surfaces. The development according to the invention has the advantage that minima needing support are no longer present in the geometry, to be produced by applying material in layers, of the respective first partial volume of the respective product. This simplifies the production process by forming the respective first partial volume of the respective product by layered application of material and also results in cost and time savings, since there is no longer any need for the material, the production and the removal of supporting structures, with all the associated disadvantages referred to above, also in respect of product quality. For essential supports for certain products and product geometries that are also required in the method according to the invention, for example in the production of auxiliary dental parts in the form of bridges, it is possible to apply support algorithms and hence fully automatic support.

It has been found in this regard that high-quality products, especially with relatively large proportions of solid volumes, can be formed by the method according to the invention. This is achieved by locating the solid volume parts in the respective second partial volume. The solid volume parts can then be produced in an advantageous manner, for example by casting the base plate, then cutting them from the base plate by machining.

The invention is preferably characterized in that the reference mark is formed on the base plate. It is particularly preferred when the reference mark is formed as a defined surface of the base plate, as a defined periphery of the base plate and as a notch in the periphery of the base plate.

The reference mark may also be embodied, for example, as a notch or embossment on the base plate, which preferably engages with a matching embossment or notch in a device for the layered application of material to form a structure, and/or in a cutting out device, in such a way that the position of the base plate is clearly defined by its three-dimensional coordinates. The dimensions of the base plate itself may serve as a reference mark by interaction with respective device features. More particularly, it is possible to provide three reference points or reference areas, preferably a periphery of the base plate, a surface of the base plate and a notch in the periphery of the base plate.

Alternatively or additionally, the invention can be developed by forming the reference mark at a structure manufactured by applying material in layers. The reference mark is preferably formed at the respective first partial volume of one or more of the products, i.e., is integrally formed at the respective first partial volume of one or more of the products in the case of layered application of material, and is subsequently removed. Alternatively or additionally, the reference mark may be formed as a structure on the base plate which is distinct from the at least two products, i.e., is formed on the base plate in the case of layered application of material.

The invention is also preferably developed by using the reference mark to align the unit formed by the base plate and the first volume zones when they are clamped into a specific position.

The invention is also preferably developed by using the reference mark as a clamping structure when the unit formed by the base plate and the first volume zone is clamped into a specific position. To this end, the reference mark may be formed as a dice-shaped structure at the respective first partial volume of one or more of the products and/or at the base plate, so that the unit formed by the base plate and the first volume zones can be clamped into position on the basis of this dice-shaped structure.

The method according to the invention method is preferably developed by the step of: generating data pertaining to the respective first partial volume of the products for forming the respective first partial volume by layered application of material, and/or generating data pertaining to the respective second partial volume of the products for cutting the respective second partial volume from the base plate.

A method for manufacturing products by applying material in layers works with geometrical data of the products. On the basis of these geometrical data of the products, the zones in the individual layers of curable material to be selectively cured are defined in order to create the geometry of the products as cured material. In order to carry out the method according to the invention, it is preferred that the data of the products to be manufactured are processed in such a way that data pertaining to a respective first partial volume of the respective product are generated which represent the geometry of the respective first partial volume of the respective product to be manufactured by applying material in layers. It is necessary here to define where the boundary between a respective first partial volume and a respective second partial volume of the respective product is to run. Criteria such as the required dimensional accuracy of the surface and the shape of the contour in relation to required supports must be taken into consideration in this regard. It is preferred that product parts involving high standards of dimensional accuracy, contour accuracy and surface quality and/or with a geometry that requires supports are defined as a respective second partial volume of the respective product.

The part of the respective product to be embodied as a respective second partial volume within the base plate need not be produced by applying material in layers. Data for the application of material in layers need only be generated for the respective first partial volume of the respective product. However, the interface between a respective first and a respective second partial volume of the respective product defines the zones of the respective first layer to be applied and to be selectively cured, since the cross-sectional areas of a respective first and a respective second partial volume substantially match each other at the interface.

When data are processed, it is preferred that data pertaining to the respective second partial volume of the product be generated which define which volume zones of the base plate are to be removed in the step of cutting the respective second partial volume of the product from the base plate and which geometry of the respective second partial volume of the product is to be cut by removing base plate material. The data are preferably generated in such a form that they can be transferred if necessary to another device, for example a CNC milling machine, which cuts the respective second partial volume of the product from the base plate.

Another aspect of the invention relates to a device for manufacturing products by applying material in layers, comprising means for applying a layer of a curable material to a base plate and means for selectively curing predetermined zones of the applied layer on the basis of geometrical data of the products, characterized by means for generating data pertaining to a respective first partial volume of the product for forming the respective first partial volume by layered application of material, and/or means for generating data pertaining to a respective second partial volume of the product for cutting the respective second partial volume from the base plate.

The device according to the invention for manufacturing products by applying material in layers differs from prior art devices for manufacturing products by applying material in layers in the device is adapted to process the data representing the products in such a way that data pertaining to the respective first partial volume of the respective product can be generated which permit the application of material in layer according to the geometrical data of the respective first partial volume of the products. The device is alternatively or additionally adapted to process the data of the products being manufactured, in such a way that data pertaining to the respective second partial volume of the products are generated which permit the respective second partial volume of the products to be cut from the base plate. The data required for cutting the respective second partial volume from the base plate are preferably available in a form that allows said data to be transferred to a device for cutting the respective second partial volume from the base plate, for example a CNC milling machine. The device is preferably developed in such a way that, with regard to the method, it can carry out preferred developments of the method that are described. Reference is made to the respective features and advantages as described in the foregoing.

The invention also relates to a device arrangement for manufacturing products by applying material partially in layers, said device arrangement comprising a first device for layered application of material to form a respective first partial volume of the products, comprising means for applying a layer of a curable material to a base plate and means for selectively curing predetermined zones of the applied layer on the basis of geometrical data of the products, characterized by a second device for cutting a respective second partial volume of the products from the base plate.

The device arrangement according to the invention comprises a first device for layered application of material to form a respective first partial volume of the products, and a second device for cutting a respective second partial volume of the products from the base plate, wherein the products to be manufactured are preferably subjected to initial processing by the first device for layered application of material and subsequently processed by the second device for cutting the respective second partial volume of the products. The device arrangement according to the invention is preferably developed in such a way that it is suitable for carrying out the steps of the method as described above, and for carrying out the further developments of the method. Reference is made to the respective features and advantages of the method as described in the foregoing.

Another aspect of the invention relates to the use of a device for layered construction of products to perform the method described in the foregoing, or its further developments, or in the device arrangement described above.

The invention shall now be described with reference to the attached Figure.

FIG. 1 shows two products 200, 300 formed on a base 100, which have already been partially manufactured, and with the rest still to be manufactured by the method according to the invention. First partial volumes of products 201, 301 have been manufactured on base plate 100 by applying layers of material. A first layer of a curable material was first applied to the base plate 100 initially provided. Predetermined zones of the first layer applied were selectively cured on the basis of geometrical data of the product. Further layers were applied to the first layer and cured until the desired geometry of the first partial volumes of products 201, 301, as shown in FIG. 1, was generated. Finally, the uncured material in all the layers was removed.

Second partial volumes 202, 302 are embodied as volume zones of base plate 100. In the case of products 200, 300 shown in FIG. 1, second partial volumes 202, 302 have not yet been cut from base plate 100. This is performed in a further processing step by machining, preferably by CNC milling.

Base plate 100 has a notch 101 which serves in combination with the surface and the periphery of the base plate as a reference mark for clamping the base plate in a specific position for the CNC milling step.

Base plate 100 consists of the same material as the cured first partial volumes 201, 301. The transitional cross-sectional areas 203, 303 between the respective first partial volumes 201, 301 and the respective second partial volumes 202, 302 are therefore identical in kind (but not exactly in dimensions, in most cases) to the other cross-sectional areas, not shown in FIG. 1, between the individual cured layers of the first partial volumes 201, 301 formed by applying material in layers. The dimensions of the individual cured layers correspond to the respective product geometry.

Products 200, 300 have contours 201b, 301b and upper surfaces 201a, 301a in the view shown in FIG. 1, which meet the requirements in respect of dimensional accuracy, contour accuracy and surface quality that can be achieved with prior art methods for applying material in layers. The second partial volumes 202, 302 have contours 202a, 302a which must satisfy higher standards in respect of dimensional accuracy, contour accuracy and surface quality. Contours 202a, 302a are preferably occlusal contours comprising a solid material portion, as shown here in FIG. 1, or, for example, contours of a contact surface for an implant. These higher standards in respect of dimensional accuracy, contour accuracy and surface quality can be achieved by the subsequent cutting of the second partial volumes 202, 302 from the base plate, in particular by machining, for example by milling contours 202a, 302a.

Product 200 also has an occlusal contour which also has an indentation 202b. As shown in FIG. 1, this indentation 202b likewise lies inside base plate 100, so no supports are needed in this region. This reduces not only the production costs but also the production time, and can improve the product quality.

A preferred example of a manufacturing process according to the invention proceeds as follows:

A base plate 100 if firstly provided, for example by casting and subsequently curing molten material and subjecting it, if necessary, to further finishing or processing, for example when a large base plate is to be subdivided into several small base plates. Base plate 100 is then clamped into a first device for manufacturing a product 200, 300 by applying material at least partially in layers. For this purpose, base plate 100 has a notch which in combination with the periphery and the surface of base plate 100 forms reference areas and permits the position of the base plate 100 to be defined three-dimensionally.

After defining where the boundary between first and second partial volumes products 200, 300 is to run, data processing means of the first device generate data pertaining to the first partial volumes 201, 301 of products 200, 300 for forming the respective first partial volumes 201, 301 by layered application of material. The product zones are preferably placed as second partial volumes 202, 302 in base plate 100, surfaces 202a, 302a of which volumes must meet special requirements, and which comprise a larger proportion of solid volume.

The data processing means also generate data pertaining to the second partial volumes 202, 302 of products 200, 300, for cutting the second partial volumes 202, 302 from base plate 100. This step may be carried out separately from generating the data pertaining to the first partial volumes 201, 301 for layered application of material. The generation of data pertaining to the first partial volumes 201, 301 for layered application of material and the generation of data pertaining to the second partial volumes 202, 302 for cutting the second partial volumes 202, 302 from base plate 100 is preferably carried out jointly or consecutively.

By means of the first device, a first layer of a curable material is now applied to base plate 100. On the basis of the geometrical data of product 200, 300, predetermined zones of the applied layer are selectively cured. The cured layer and base plate 100 consist of the same material.

Another layer of the curable material is then applied to the cured first layer under it, and predetermined zones of the newly applied layer, in turn, are selectively cured on the basis of the geometrical data of product 200, 300. Yet another layer of the curable material is applied to the latter cured layer, and predetermined zones of this newly applied layer are selectively cured, in turn, on the basis of the geometrical data of product 200, 300. As many layers of the curable material as are required to completely manufacture the first partial volumes 201, 301 are applied in the same manner, i.e., the geometry of the first partial volumes 201, 301 are formed of cured material by applying the material in layers.

Base plate 100, with the first partial volumes 201, 301 integrally joined to it, is then removed from the device for manufacturing a product 200, 300 by applying material at least partially in layers, and supplied to a second device for cutting the second partial volumes 202, 302 of the product from base plate 100. The second device is a CNC milling machine, for example.

Base plate 100, with the first partial volumes 201, 301 integrally joined to it, is clamped into the second device. The aforementioned reference areas of base plate 100 are again used for defining the position of base plate 100 three-dimensionally.

The generated data pertaining to the second partial volumes 202, 302 for cutting the second partial volumes 202, 302 from base plate 100 are also transferred to the second device.

On the basis of these data and the definition of the position of base plate 100 by the reference areas, the second device now removes those regions of base plate 100 belonging to products 200, 300, thereby cutting the second partial volumes 202, 302 of products 200, 300 from base plate 100 by machining.

The invention claimed is:

1. A method for manufacturing products by applying material at least partially in layers, in particular by selective laser melting, said method comprising the steps of:
    (a) providing a base plate made of the same material as the product,
    (b) applying a layer of a curable material,
    (c) selectively curing predetermined zones of the applied layer on a basis of geometrical data of at least two separate products by said selective laser melting,
    (d) repeating steps (b) and (c) until a geometry of a respective first partial volume of the respective product has been created in a form of cured material,
    (e) removing a portion of the material that has not cured, wherein a respective second partial volume of the respective product is formed as a volume zone of the base plate and,
    further comprising the steps:
        providing a reference mark,
        clamping a unit formed by the base plate and the first volume zone into a specific position by means of the reference mark,
        cutting the respective second partial volume of the respective product from the base plate, preferably by machining, in particular by CNC milling, wherein the products comprise one or more tooth replacement parts, and that the respective second partial volume of one or more of the tooth replacement parts comprises occlusal product segments, in particular masticating surfaces.

2. The method of claim 1, wherein the reference mark is formed on the base plate.

3. The method of claim 2, wherein the reference mark is formed as a defined surface of the base plate, as a defined periphery of the base plate, or as a notch in the periphery of the base plate.

4. The method of claim 1, wherein the reference mark is formed at a structure manufactured by applying material in layers.

5. The method of claim 4, wherein the manufactured structure comprises the respective first partial volume of one or more of the products and is subsequently removed.

6. The method of claim 4, wherein the manufactured structure is formed as a structure on the base plate which is distinct from the at least two products.

7. The method of claim 1, wherein the reference mark is used to align the clamped unit.

8. The method of claim 4, wherein the reference mark is used as a clamping structure configured to clamp the unit into the specific position.

9. The method of claim 1, further comprising the step of:
generating data pertaining to the respective first partial volume of the products for forming the respective first partial volume by layered application of material, and/or generating data pertaining to the respective second partial volume of the products for cutting the respective second partial volume from the base plate.

\* \* \* \* \*